United States Patent
Osawa

(10) Patent No.: US 8,934,966 B2
(45) Date of Patent: Jan. 13, 2015

(54) BIOELECTRICAL IMPEDANCE MEASURING APPARATUS

(75) Inventor: Masato Osawa, Auderghem (BE)

(73) Assignee: Olympus Corporation, Tokyo (JP)

(*) Notice: Subject to any disclaimer, the term of this patent is extended or adjusted under 35 U.S.C. 154(b) by 547 days.

(21) Appl. No.: 13/355,263

(22) Filed: Jan. 20, 2012

(65) Prior Publication Data

US 2012/0194203 A1    Aug. 2, 2012

(30) Foreign Application Priority Data

Jan. 31, 2011  (JP) .................................. 2011-018201

(51) Int. Cl.
  *A61B 5/00*    (2006.01)
(52) U.S. Cl.
  USPC ....................................................... 600/547
(58) Field of Classification Search
  USPC ....................................................... 600/547
  See application file for complete search history.

(56) References Cited

U.S. PATENT DOCUMENTS

| 7,869,866 B2* | 1/2011 | Loriga et al. .................. 600/547 |
| 7,970,462 B2* | 6/2011 | Lefkov et al. ................. 600/547 |
| 8,332,026 B2* | 12/2012 | Cha et al. ...................... 600/547 |
| 8,610,022 B2* | 12/2013 | Rock ............................... 219/50 |
| 8,682,424 B2* | 3/2014 | Tsoglin et al. ................ 600/547 |
| 8,761,871 B2* | 6/2014 | Blomqvist .................... 600/547 |

FOREIGN PATENT DOCUMENTS

JP    2008-168120 A    7/2008

* cited by examiner

*Primary Examiner* — Max Hindenburg
(74) *Attorney, Agent, or Firm* — Westerman, Hattori, Daniels & Adrian, LLP

(57) ABSTRACT

A bioelectrical impedance measuring apparatus may include an impedance measuring unit configured to provide an inspection current based on a predetermined current to a living body, and obtain an inspection voltage corresponding to an impedance of the living body, an amplification unit configured to amplify the inspection voltage with reference to a correction voltage, an AD converter configured to AD-convert an output of the amplification unit, and a control unit configured to control the inspection current and the correction voltage based on an AD-converted result of the AD converter such that the output of the amplification unit is within an input dynamic range of the AD converter, and calculate an impedance average of the living body and an impedance variation of the living body based on the predetermined current, the correction voltage and the AD-converted result.

4 Claims, 8 Drawing Sheets

BIOELECTRICAL IMPEDANCE MEASURING APPARATUS

BACKGROUND OF THE INVENTION

1. Field of the Invention

The present invention relates to a bioelectrical impedance measuring apparatus that can be mounted on an implantable medical instrument.

Priority is claimed on Japanese Patent Application No. 2011-018201, filed Jan. 31, 2011, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

A method disclosed in Japanese Unexamined Patent Application, First Publication No. 2008-168120 is well known as a method of precisely calculating a cardiac output and a pulmonary artery wedge pressure of a living body. FIG. 11 shows a configuration of a cardiac output monitor system disclosed in Japanese Unexamined Patent Application, First Publication No. 2008-168120. Hereinafter, a schematic operation of the cardiac output monitor system will be described with reference to FIG. 11. In addition, the configuration disclosed in Japanese Unexamined Patent Application, First Publication No. 2008-168120 is shown in FIG. 11 with convenient modifications of the following description added.

The cardiac output monitor system calculates a cardiac output and a pulmonary artery wedge pressure using an impedance signal that can be obtained by applying an alternate current to the heart. An extracting unit 11 extracts a minimum impedance signal Zmin, a maximum impedance signal Zmax, and an impedance average value signal Zmean based on an impedance signal received from a receiving unit 10.

A solid tissue derived impedance estimating unit 12 estimates a solid tissue derived impedance Zs based on a data set of a plurality of cardiac cycles including a maximum value and a minimum value in one cardiac cycle of an impedance signal that can be obtained within a predetermined time after injecting a hypertonic salt solution during a pulmonary circulation. A cardiac output calculating unit 13 precisely calculates a cardiac output using the following equation (A):

$$CO = k \cdot (1/(Zmin-Zs) - 1/(Zmax-Zs)) \cdot HR \quad (A)$$

where CO: cardiac output, k: correction factor, and HR: heart rate.

A pulmonary artery wedge pressure calculating unit 14 precisely calculates a pulmonary artery wedge pressure using the following equation (B):

$$PAWP = A \times C/(Zmean-Zs) - CO \times B \quad (B)$$

where PAWP: pulmonary artery wedge pressure, and A, B, C: correction factors.

In general, the value of the impedance average value signal Zmean of the heart is known to be about 500Ω, the value of the minimum impedance signal Zmin is known to be 500 Ω−5Ω, and a value of the maximum impedance signal Zmax is known to be about 500 Ω+5Ω. That is, the difference between the impedance average value signal Zmean and the minimum impedance signal Zmin or the maximum impedance signal Zmax is about ±1% with respect to the impedance average value signal of the heart.

When a voltage corresponding to an impedance signal of the heart is to be applied to an analog-digital (AD) converter to perform the calculation disclosed in the above equations (A) and (B), in order to detect an impedance-varying signal Zac, which is a differential between the impedance average value signal Zmean, the minimum impedance signal Zmin, and the maximum impedance signal Zmax of the heart caused by the cardiac output, a large number of effective bits is needed by the AD converter. This is shown in FIG. 12. In addition, an impedance average voltage Vmean, an impedance-varying voltage Vac, an impedance maximum voltage Vman, and an impedance minimum voltage Vmin in FIG. 12 are voltage signals corresponding to the impedance average value signal Zmean, the impedance-varying signal Zac, the maximum impedance signal Zmax, and the minimum impedance signal Zmin, respectively. Further, 1 LSB is a minimum resolution of the AD converter.

The following equation (C) is a relational expression representing power consumption Pd of the AD converter. Here, fc: sampling frequency, and ENOB: the number of effective bits. Equation (C) represents that the power consumption Pd of the AD converter is in proportion to a product of the sampling frequency fc and $2^{ENOB}$.

$$P_d \propto f_C \times 2^{ENOB} \quad (C)$$

As can be seen from equation (C), the AD converter having a large number of effective bits requires a large amount of power. This means that the cardiac output monitor system, on which the AD converter is mounted, also requires a large amount of power. Thus, the time that an implantable medical instrument can be implanted may be shortened, on which the cardiac output monitor system is mounted.

SUMMARY

The present invention has been made in view of the above-described circumstances, and an object of the invention is to provide a bioelectrical impedance measuring apparatus capable of suppressing power consumption and precisely detecting an average value of a bioelectrical impedance and a variation of the bioelectrical impedance.

A bioelectrical impedance measuring apparatus may include: an impedance measuring unit configured to provide an inspection current based on a predetermined current to a living body, and obtain an inspection voltage corresponding to an impedance of the living body; an amplification unit configured to amplify the inspection voltage with reference to a correction voltage; an AD converter configured to AD-convert an output of the amplification unit; and a control unit configured to control the inspection current and the correction voltage based on an AD-converted result of the AD converter such that the output of the amplification unit is within an input dynamic range of the AD converter, and calculate an impedance average of the living body and an impedance variation of the living body based on the predetermined current, the correction voltage and the AD-converted result.

The amplification unit may include a lowpass filter.

The impedance measuring unit may include: a modulation circuit configured to modulate the predetermined current into a modulated signal having a modulation frequency higher than a variable frequency of a bioelectrical impedance to generate the inspection current; and a demodulation circuit configured to demodulate a measurement voltage that can be obtained by applying the inspection current to the living body to generate the inspection voltage. The lowpass filter may have a cutoff frequency smaller than twice the modulation frequency of the modulation circuit and larger than the variable frequency of the bioelectrical impedance.

The amplification unit may include: a first operational amplifier having a first non-inversion input terminal, a first inversion input terminal and a first output terminal, the inspection voltage being input into the first non-inversion input terminal, to which the first inversion input terminal and the first output terminal are connected; a second operational amplifier having a second non-inversion input terminal, a second inversion input terminal and a second output terminal, the correction voltage being input into the second non-inversion input terminal; an input resistor having a first terminal and a second terminal, the first terminal being connected to the first output terminal of the first operational amplifier and the second terminal being connected to the second inversion input terminal of the second operational amplifier; a feedback resistor having a third terminal and a fourth terminal, the third terminal being connected to the second inversion input terminal of the second operational amplifier and the fourth terminal being connected to the second output terminal of the second operational amplifier; and a feedback capacitor having a fifth terminal and a sixth terminal, the fifth terminal being connected to the second inversion input terminal of the second operational amplifier and the sixth terminal being connected to the second output terminal of the second operational amplifier.

According to the present invention, a voltage corresponding to a bioelectrical impedance variation can be amplified with a high gain by controlling an inspection current and a correction voltage such that an output of an amplification unit is within an input dynamic range of the AD converter based on an AD conversion result of the AD converter. Accordingly, since a voltage corresponding to the bioelectrical impedance variation can be obtained with substantial resolution even when the AD converter having a small number of effective bits is used, an average of the bioelectrical impedance and the bioelectrical impedance variation can be precisely detected while suppressing power consumption.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated for explanatory purpose.

Bioelectrical Impedance Measuring Apparatus

Figure 1:
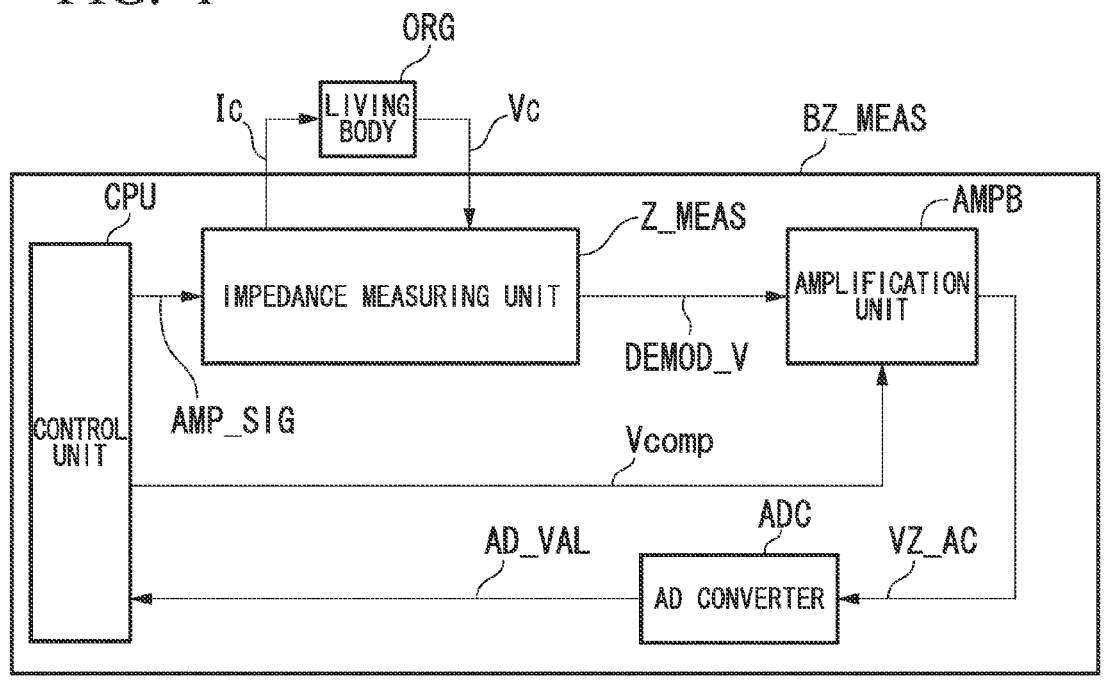
FIG. 1 is a block diagram illustrating a configuration of a bioelectrical impedance measuring apparatus in accordance with a first preferred embodiment of the present invention.

FIG. 1 shows a configuration of a bioelectrical impedance measuring apparatus in accordance with a first preferred embodiment of the present invention. The bioelectrical impedance measuring apparatus BZ_MEAS shown in FIG. 1 includes an impedance measuring unit Z_MEAS, an amplification unit AMPB, an AD converter ADC, and a control unit CPU.

The impedance measuring unit Z_MEAS is connected to a first lead wire configured to apply an inspection current Ic to a living body ORG of an object to be measured, and a second lead wire configured to detect an inspection voltage Vc generated in the living body ORG. An amplitude control signal AMP_SIG for controlling the magnitude of the inspection current Ic is input into the impedance measuring unit Z_MEAS. In addition, the impedance measuring unit Z_MEAS is also connected to the amplification unit AMPB. The impedance measuring unit Z_MEAS flows the inspection current Ic, in which a constant current is modulated, to the living body ORG, obtains the inspection voltage Vc generated in the living body ORG, and outputs a demodulated voltage DEMOD_V, which is a voltage signal in response to the impedance of the living body ORG, to the amplification unit AMPB.

The amplification unit AMPB is connected to the impedance measuring unit Z_MEAS, the analog-to-digital (AD) converter ADC and the control unit CPU to amplify the demodulated voltage DEMOD_V input from the impedance measuring unit Z_MEAS to a predetermined magnification with reference to a correction voltage Vcomp, and output an impedance-varying voltage VZ_AC in response to variation of the impedance of the living body ORG to the AD converter ADC.

The AD converter ADC is connected to the amplification unit AMPB and the control unit CPU to AD-convert the impedance-varying voltage VZ_AC input from the amplification unit AMPB, outputting the AD-conversion result AD_VAL to the control unit CPU.

The control unit CPU is connected to the amplification unit AMPB, the impedance measuring unit Z_MEAS and the AD converter ADC. The control unit CPU outputs the amplitude control signal AMP_SIG for controlling the magnitude of the inspection current Ic to the impedance measuring unit Z_MEAS. In addition, the control unit CPU adjusts the correction voltage Vcomp and the amplitude control signal AMP_SIG output to the amplification unit AMPB according to the AD-conversion result AD_VAL input from the AD converter ADC, and simultaneously, calculates values of the impedance average value signal Zmean and the impedance-varying signal Zac of the living body using values of the amplitude control signal AMP_SIG, the AD-conversion result AD_VAL and the correction voltage VCOMP.

Impedance Measuring Unit

Figure 2:
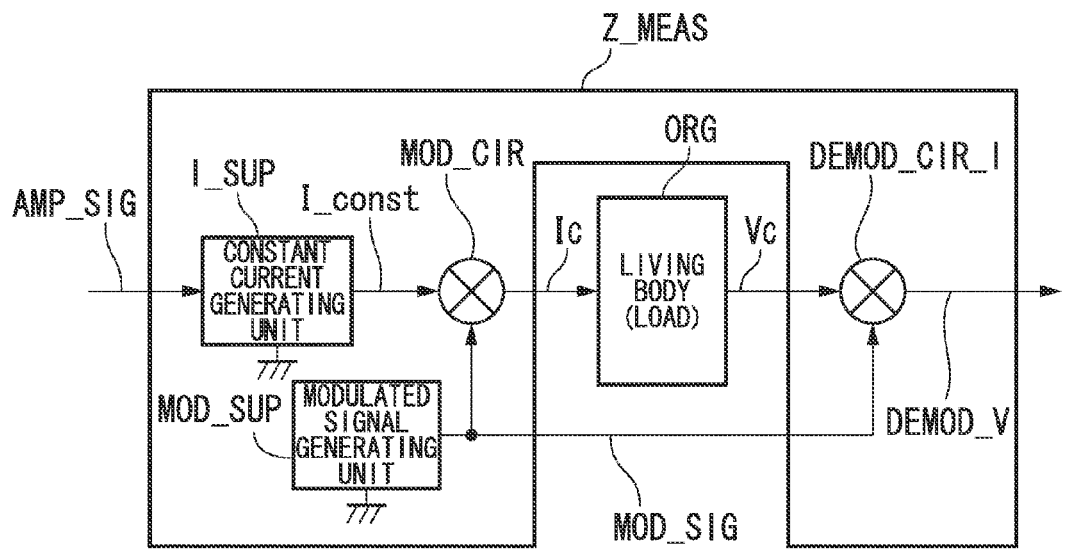
FIG. 2 is a block diagram illustrating a configuration of an impedance measuring unit in accordance with the first preferred embodiment of the present invention.
Figure 3:
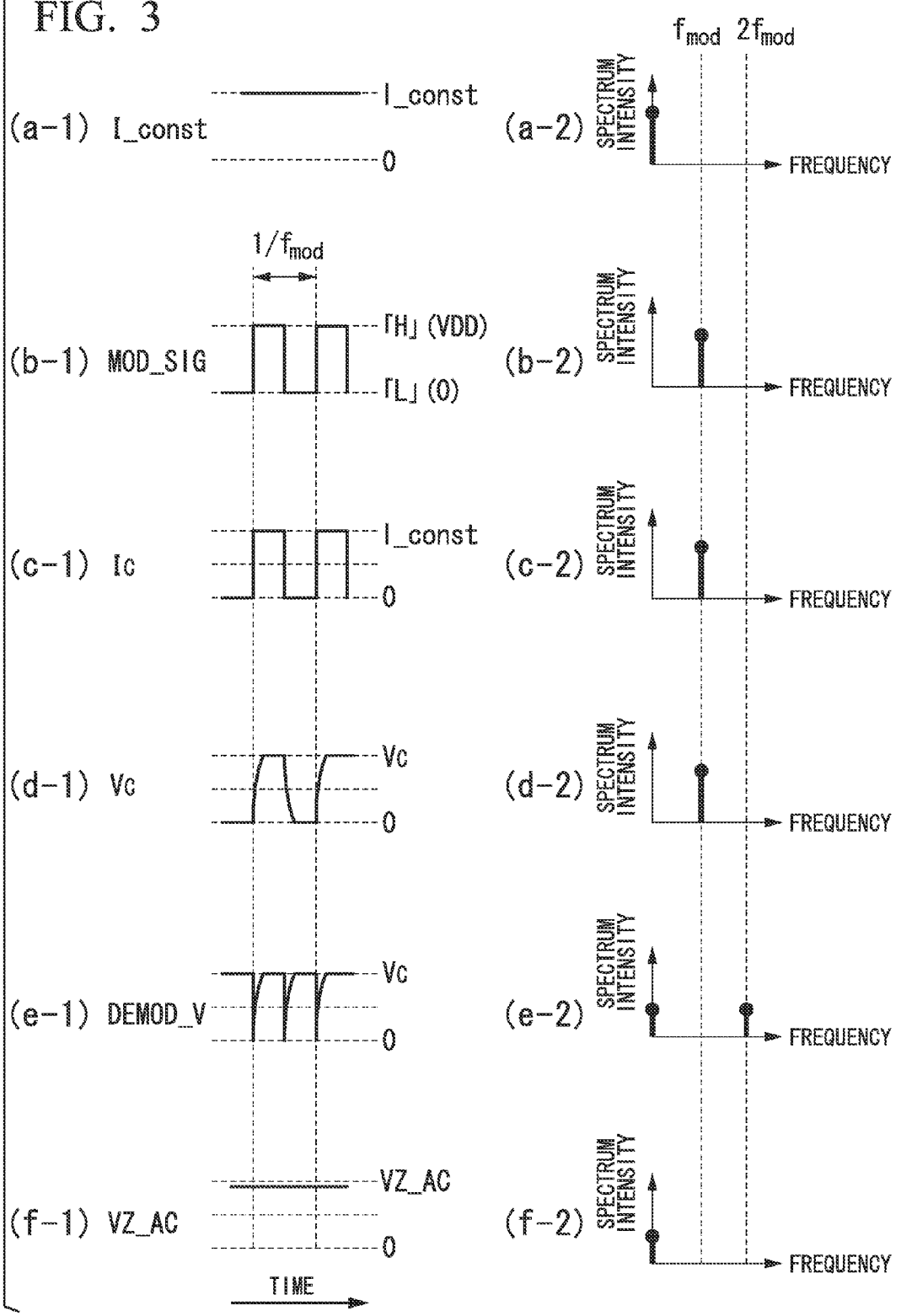
FIG. 3 is a view illustrating waveform and frequency components of important signals of the impedance measuring unit in accordance with the first preferred embodiment of the present invention.
Figure 4:
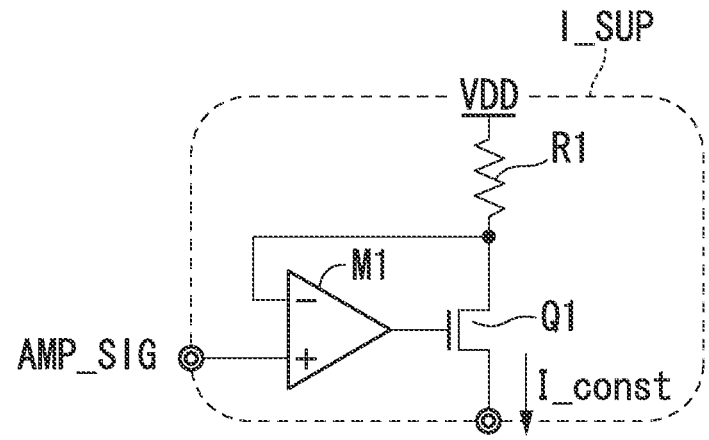
FIG. 4 is a circuit diagram illustrating a configuration of a constant current generating unit of the impedance measuring unit in accordance with the first preferred embodiment of the present invention.
Figure 5:
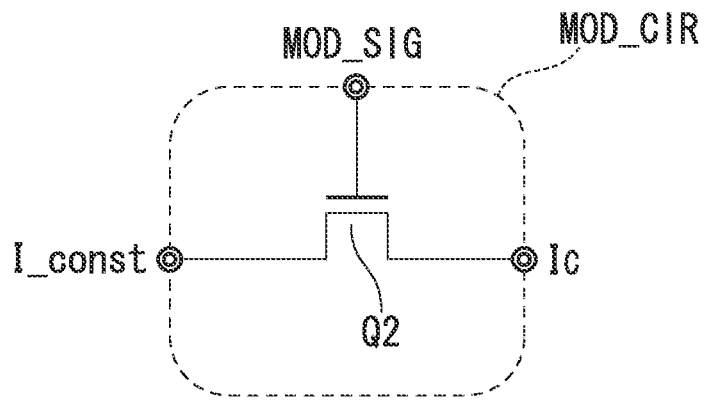
FIG. 5 is a circuit diagram illustrating a configuration of a modulation circuit of the impedance measuring unit in accordance with the first preferred embodiment of the present invention.
Figure 6:
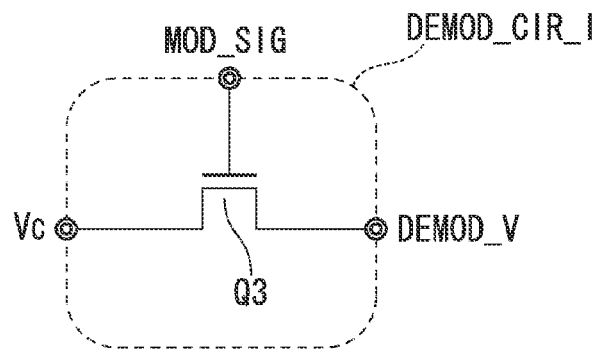
FIG. 6 is a circuit diagram illustrating a configuration of a demodulation circuit of the impedance measuring unit in accordance with the first preferred embodiment of the present invention.

Hereinafter, an operation of the impedance measuring unit Z_MEAS will be described in detail with reference to FIGS. 2, 3, 4, 5 and 6. FIG. 2 shows a configuration of the impedance measuring unit Z_MEAS. FIG. 3 shows waveform and frequency components of important signals of the impedance measuring unit Z_MEAS. (a-1), (b-1), (c-1), (d-1), (e-1) and (f-1) of FIG. 3 show waveforms of the following important signals, horizontal axes representing times and vertical axes representing amplitudes of the signals. In addition, (a-2), (b-2), (c-2), (d-2), (e-2) and (f-2) of FIG. 3 show frequency components of the important signals, horizontal axes representing frequencies and vertical axes representing spectrum intensities. FIG. 4 shows a configuration of a constant current generating unit of the impedance measuring unit Z_MEAS. FIG. 5 shows a configuration of a modulation circuit of the impedance measuring unit Z_MEAS. FIG. 6 shows a configuration of a demodulation circuit of the impedance measuring unit Z_MEAS.

Hereinafter, an operation of the impedance measuring unit Z_MEAS will be described basically with reference to FIG. 2. Also, FIGS. 3, 4, 5 and 6 will be used as necessary. As shown in FIG. 2, the impedance measuring unit Z_MEAS includes a constant current generating unit I_SUP, a modulation circuit MOD_CIR, a modulated signal generating unit MOD_SUP, and a demodulation circuit DEMOD_CIR_I.

The constant current generating unit I_SUP is connected to the control unit CPU and the modulation circuit MOD_CIR to output a constant current I_const in response to the amplitude control signal AMP_SIG input from the control unit CPU to the modulation circuit MOD_CIR. Specifically, as shown in FIG. 4, the constant current generating unit I_SUP includes a constant current circuit having an operational amplifier M1, a resistor R1 and an NMOS transistor Q1 to output a constant current I_const represented by the following equation (1). Here, VDD represents a power voltage supplied to the constant current generating unit I_SUP, VAMP_SIG represents a voltage of the amplitude control signal AMP_SIG, and R_const represents a resistance value of the resistor R1.

$$I\_const = (VDD - VAMP\_SIG)/R\_const \quad (1)$$

In addition, a waveform of the constant current I_const is as shown in (a-1) of FIG. 3 and the constant current I_const shows a constant value regardless of a time. Further, a frequency component of the constant current I_const is as shown in (a-2) of FIG. 3. The constant current I_const has a peak of a spectrum at a frequency 0, which is constant regardless of time.

The modulated signal generating unit MOD_SUP is connected to the modulation circuit MOD_CIR to generate the modulated signal MOD_SIG, which is a square wave in which a signal level is converted to a high level (hereinafter referred to as H) and a low level (hereinafter referred to as L), at a modulation frequency fmod higher than a variable frequency forg of the bioelectrical impedance to be measured, and output the modulated signal MOD_SIG to the modulation circuit MOD_CIR and the demodulation circuit DEMOD_CIF_I. In addition, a waveform of the modulated signal MOD_SIG is as shown in (b-1) of FIG. 3. H and L of the modulated signal MOD_SIG are switched at a cycle of 1/fmod. A spectrum of the modulated signal MOD_SIG has a peak at a modulation frequency fmod as shown in (b-2) of FIG. 3.

When the modulated signal MOD_SIG, which is a square wave, is provided as f(t), a Fourier expansion is represented as the following equation (2):

$$f(t) = (VDD/2) \cdot \{\sin(2\pi \cdot f mod \cdot t) + (\tfrac{1}{3}) \cdot \sin(3 \cdot 2\pi \cdot f mod \cdot t) + (\tfrac{1}{5}) \cdot \sin(5 \cdot 2\pi \cdot f mod \cdot t) + \ldots \} \quad (2)$$

For the purpose of simple explanation, (b-2) of FIG. 3 shows only the spectrum component of a fundamental wave $\sin(2\pi \cdot fmod \cdot t)$ constituting the modulated signal MOD_SIG. In order to explain the operational principle of the bioelectrical impedance measuring apparatus BZ_MEAS, since discussion of the fundamental wave component only is sufficient, consideration of the fundamental wave component only will be described below.

The modulation circuit MOD_CIR is connected to the constant current generating unit I_SUP, the modulated signal generating unit MOD_SUP, and the living body ORG to output a signal obtained by multiplying the constant current I_const and the modulated signal MOD_SIG to the living body ORG as an inspection current Ic. Specifically, the modulation circuit MOD_CIR, which includes an analog switch Q2 shown in FIG. 5, is turned ON when the modulated signal MOD_SIG is H and turned OFF when the modulated signal MOD_SIG is L. In addition, a waveform of the inspection current Ic is a square wave shown in (c-1) of FIG. 3, and a spectrum of the inspection current Ic has a peak at a modulation frequency fmod as shown in (c-2) of FIG. 3. A fundamental frequency component of the inspection current Ic is represented by the following equation (3):

$$I\_const \times \sin(2\pi \cdot fmod \cdot t) \quad (3)$$

As the inspection current Ic is applied to the living body ORG, the inspection voltage Vc provided by the following equation (4) is generated. Here, Zc represents an impedance of the living body ORG, and α represents a phase difference generated when the bioelectrical impedance is not a pure resistance component. When a capacity component or an induction coefficient component of the living body is substantially smaller than the resistance component, α may be negligible.

In addition, a waveform of the inspection voltage Vc is as shown in (d-1) of FIG. 3. A spectrum of the inspection voltage Vc has a peak at the modulation frequency fmod as shown in (d-2) of FIG. 3.

$$Vc = I\_const \times |Zc| \times \sin(2\pi \cdot fmod \cdot t + \alpha) \quad (4)$$

The demodulation circuit DEMOD_CIR_I is connected to the living body ORG, the modulated signal generating unit MOD_SUP and the amplification unit AMPB to output a signal obtained by multiplying the inspection voltage Vc and the modulated signal MOD_SIG to the amplification unit AMPB as the demodulated voltage DEMOD_V. Specifically, the demodulation circuit DEMOD_CIR_I, which includes an analog switch Q3 as shown in FIG. 6, is turned ON when the modulated signal MOD_SIG is H and turned OFF when the modulated signal MOD_SIG is L.

A fundamental frequency component of the demodulated voltage DEMOD_V is represented by the following equation (5):

$$I\_const \times Zc \times \sin(2\pi \cdot fmod \cdot t + \alpha) \times \sin 2\pi \cdot fmod \cdot t = (1/2) \times I\_const \times |Zc| \{\cos(-\alpha) - \cos(4\pi \cdot fmod \cdot t)\} \quad (5)$$

In addition, a waveform of the demodulated voltage DEMOD_V is as shown in (e-1) of FIG. 3, and a frequency component is as shown in (e-2) of FIG. 3. As can be seen from equation (5) and (e-2) of FIG. 3, the demodulated voltage DEMOD_V based on a voltage signal generated from the living body ORG has a DC component represented as a term of $\cos(-\alpha)$, and a frequency component, which is represented as a term of $-\cos(4\pi \cdot fmod \cdot t)$, in which the modulation frequency fmod is modulated twice.

Amplification Unit

Figure 7:
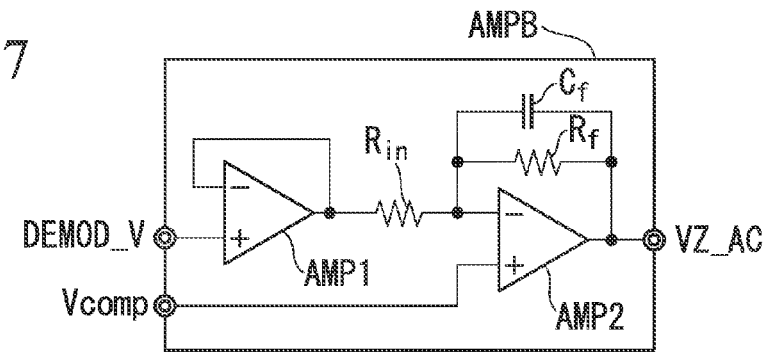
FIG. 7 is a circuit diagram illustrating a configuration of an amplification unit in accordance with the first preferred embodiment of the present invention.

Hereinafter, the amplification unit AMPB will be described with reference to FIG. 7. The amplification unit AMPB includes a first operational amplifier AMP1, a second operational amplifier AMP2, an input resistor Rin, a feedback resistor Rf, and a feedback capacitor Cf.

The demodulated signal DEMOD_V is input into a non-inversion input terminal of the first operational amplifier AMP1, and an inversion input terminal and an output terminal of the first operational amplifier AMP1 are connected to the non-inversion input terminal. A correction voltage Vcomp is input into a non-inversion input terminal of the second operational amplifier AMP2, and an impedance-varying voltage VZ_AC is output from an output terminal of the second operational amplifier AMP2. A first terminal of the input resistor Rin is connected to an output terminal of the first operational amplifier AMP1 and a second terminal of the input resistor Rin is connected to the inversion input terminal of the second operational amplifier AMP2.

A first terminal of the feedback resistor Rf is connected to the inversion input terminal of the second operational amplifier AMP2, and a second terminal of the feedback resistor Rf is connected to the output terminal of the second operational amplifier AMP2. A first terminal of the feedback capacitor Cf is connected to the inversion input terminal of the second operational amplifier AMP2, and a second terminal of the feedback capacitor Cf is connected to the output terminal of the second operational amplifier AMP2.

The first operational amplifier AMP1 is operated as a voltage follower to buffer the demodulated voltage DEMOD_V having a relatively high impedance and output the buffered demodulated voltage DEMOD_V to the first terminal of the input resistor Rin. In addition, the second operational amplifier AMP2, the input resistor Rin, the feedback resistor Rf and the feedback capacitor Cf are operated as a lowpass filter having an inversion amplification function, and a cutoff frequency $f_{LPF}$ is represented by the following equation (6).

$$f_{LPF} = \frac{1}{2\pi C_f R_f} \quad (6)$$

The cutoff frequency $f_{LPF}$ is set as a value smaller than twice the fundamental frequency of the modulation frequency fmod and larger than the variable frequency $f_{ORG}$ of the bioelectrical impedance. For this reason, a high frequency component represented as a term of $-\cos(4\pi \cdot fmod \cdot t)$ in equation (5) is removed by an operation as the lowpass filter. Accordingly, the signal amplified by the amplification unit AMPB becomes a component of $(1/2) \times I\_const \times |Zc| \{\cos(-\alpha)\}$ of equation (5). In addition, the waveform is shown in (f-1) of FIG. 3. Further, the waveform is shown as a scale corresponding to a variation time of the modulation frequency fmod, and the impedance-varying voltage VZ_AC varied in a longer cycle than a cycle based on the modulation frequency fmod is shown to be constant regardless of time.

Figure 8:
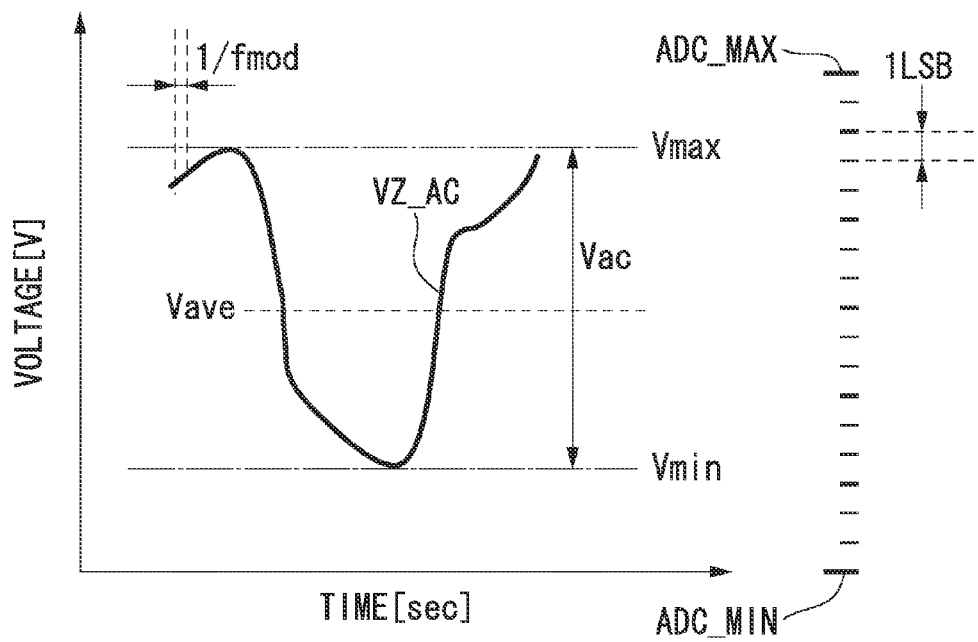
FIG. 8 is a timing chart illustrating variation of an impedance signal of heart acquired by a bioelectrical impedance measuring apparatus in accordance with the first preferred embodiment of the present invention.

An actual impedance-varying voltage VZ_AC is slowly varied at the variable frequency $f_{ORG}$ of the bioelectrical impedance as shown in FIG. 8. As shown in the spectrum of the impedance-varying voltage VZ_AC of (f-2) of FIG. 3, the frequency component of the signal output from the amplification unit AMPB has a peak around a DC component only to remove the high frequency component using the lowpass filter.

In addition, the amplification unit AMPB amplifies a signal with characteristics represented by the following equation (7). Here, Vout denotes a voltage output from the output terminal of the second operational amplifier AMP2, Vin denotes a voltage input into the first terminal of the input resistor Rin, and Vcomp denotes a voltage input into the non-inversion input terminal of the second operational amplifier AMP2.

$$V_{out} = -\frac{R_f}{R_{in}} V_{in} + \left(1 + \frac{R_f}{R_{in}}\right) V_{comp} \quad (7)$$

Here, provided that Vin=Vmean+Vac, equation (7) is converted to equation (8).

$$V_{out} = -\frac{R_f}{R_{in}}(V_{mean} + V_{ac}) + \left(1 + \frac{R_f}{R_{in}}\right) V_{comp} \quad (8)$$

$$= -\frac{R_f}{R_{in}} V_{ac} + \frac{R_f}{R_{in}}(V_{comp} - V_{mean}) + V_{comp}$$

Here, provided that a component that is constant regardless of a time is an average voltage Vave represented by equation (9), equation (10) can be obtained.

$$\frac{R_f}{R_{in}}(V_{comp} - V_{mean}) + V_{comp} = V_{ave} \quad (9)$$

$$V_{out} = -\frac{R_f}{R_{in}} V_{ac} + V_{ave} \quad (10)$$

As will be described below, the control unit CPU adjusts the correction voltage Vcomp such that the average voltage Vave is within an input voltage range (an input dynamic range) of the AD converter ADC. Accordingly, even when the impedance average voltage Vmean is any value, by adjusting the correction voltage Vcomp, the amplification unit AMPB can amplify only the impedance-varying voltage Vac $-(Rf/Rin)$ times with respect to the average voltage Vave.

That is, the control unit CPU can generate the correction voltage Vcomp represented by equation (9) to amplify the impedance-varying voltage Vac with a high gain within the input voltage range of the AD converter ADC. For this reason, even when resolution of the AD converter ADC is lowered, variation in the voltage signal corresponding to variation in the bioelectrical impedance can be measured with high resolution.

Control Unit

Figure 9:
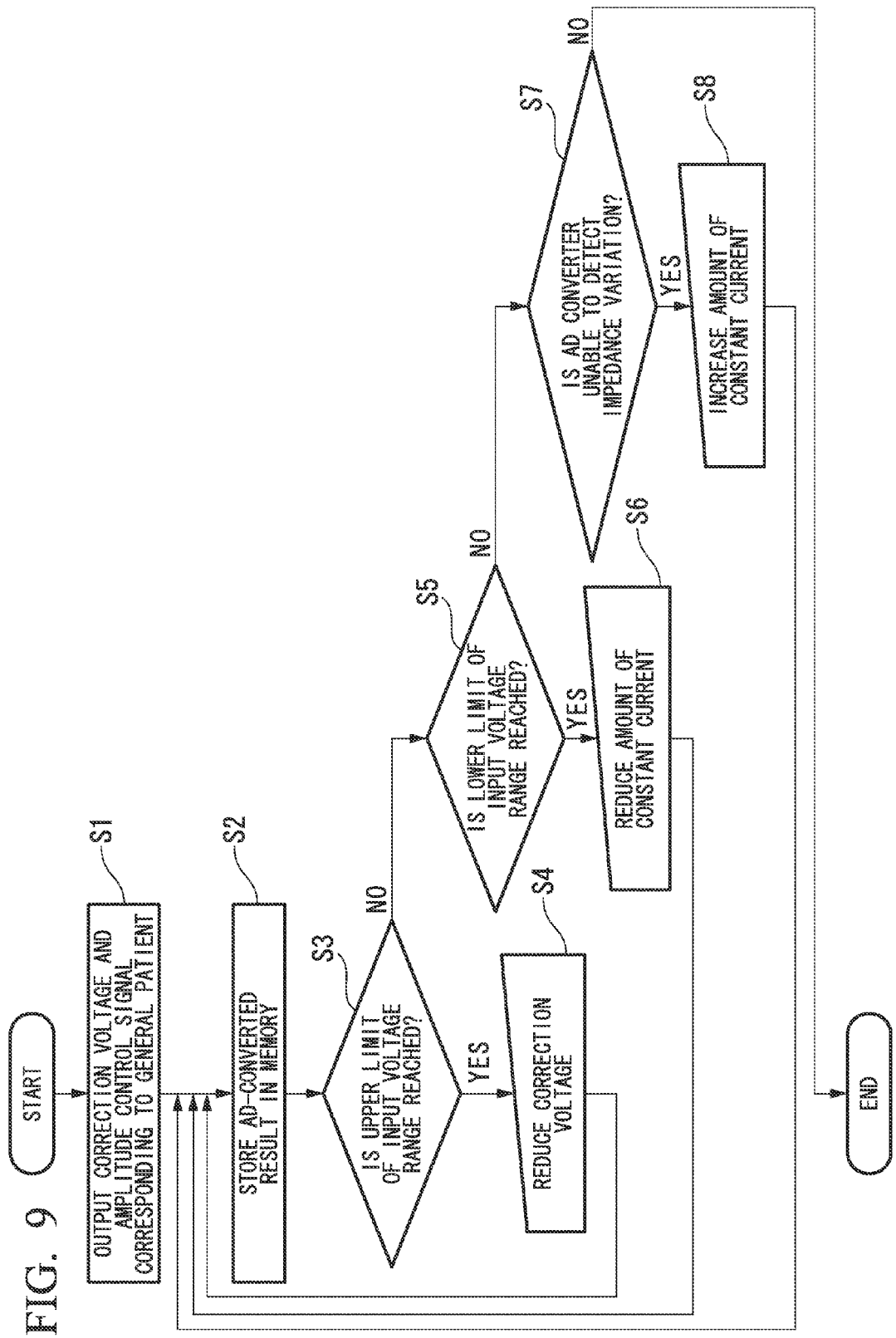
FIG. 9 is a flow chart illustrating a sequence of an operation of a control unit in accordance with the first preferred embodiment of the present invention.
Figure 10A:
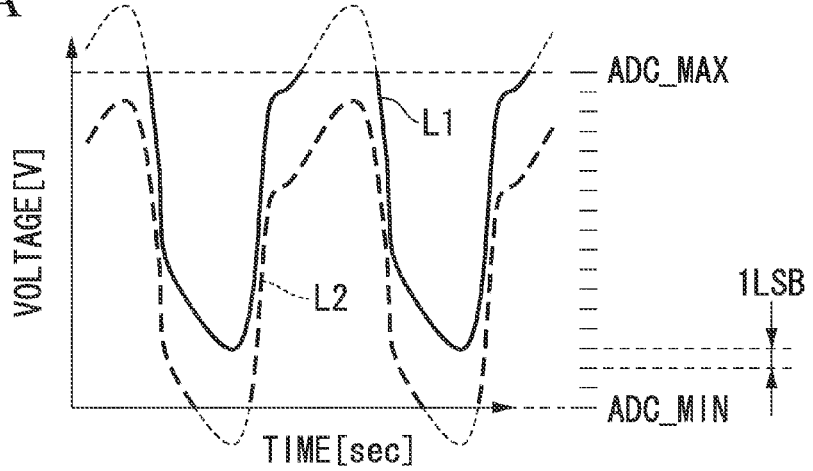
FIGS. 10A, 10B and 10C are timing charts illustrating waveforms of an impedance-varying voltage in respective steps shown in FIG. 9.
Figure 10B:
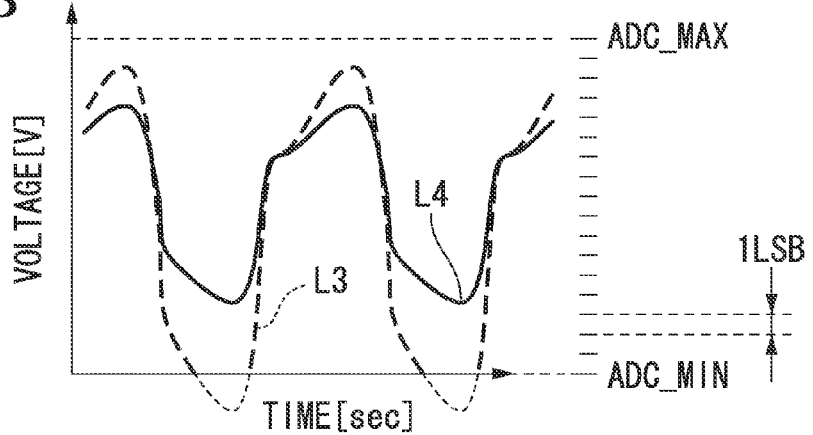
Figure 10C:
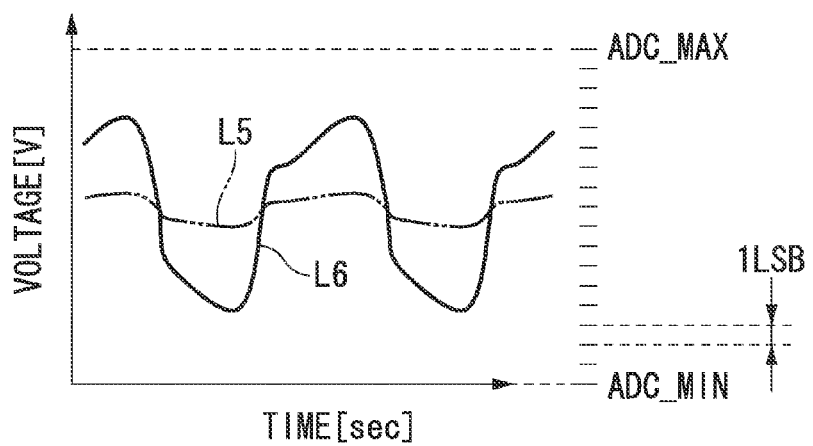
Figure 11:
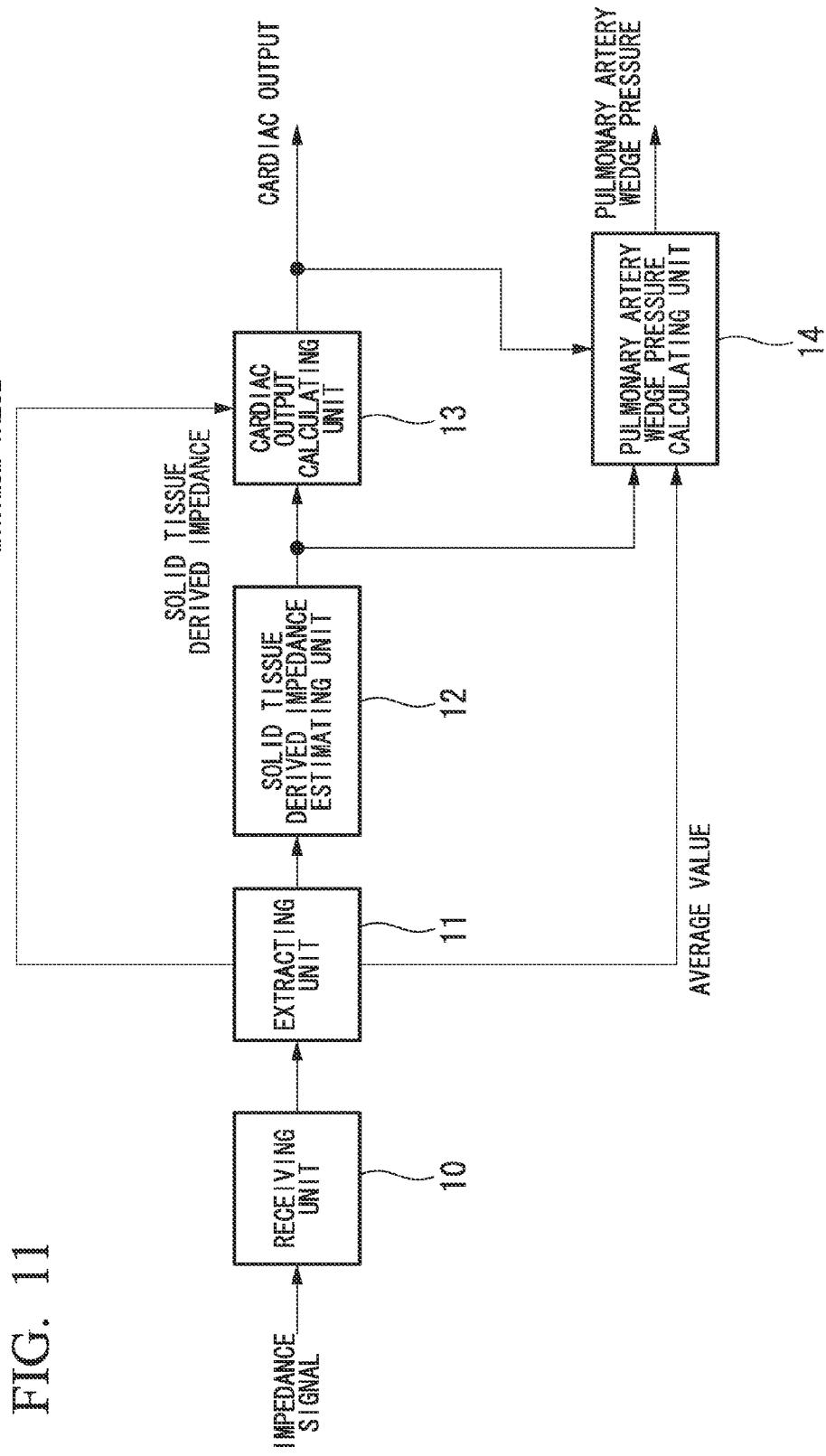
FIG. 11 is a block diagram illustrating a configuration of a cardiac output monitor system in accordance with the related art.
Figure 12:
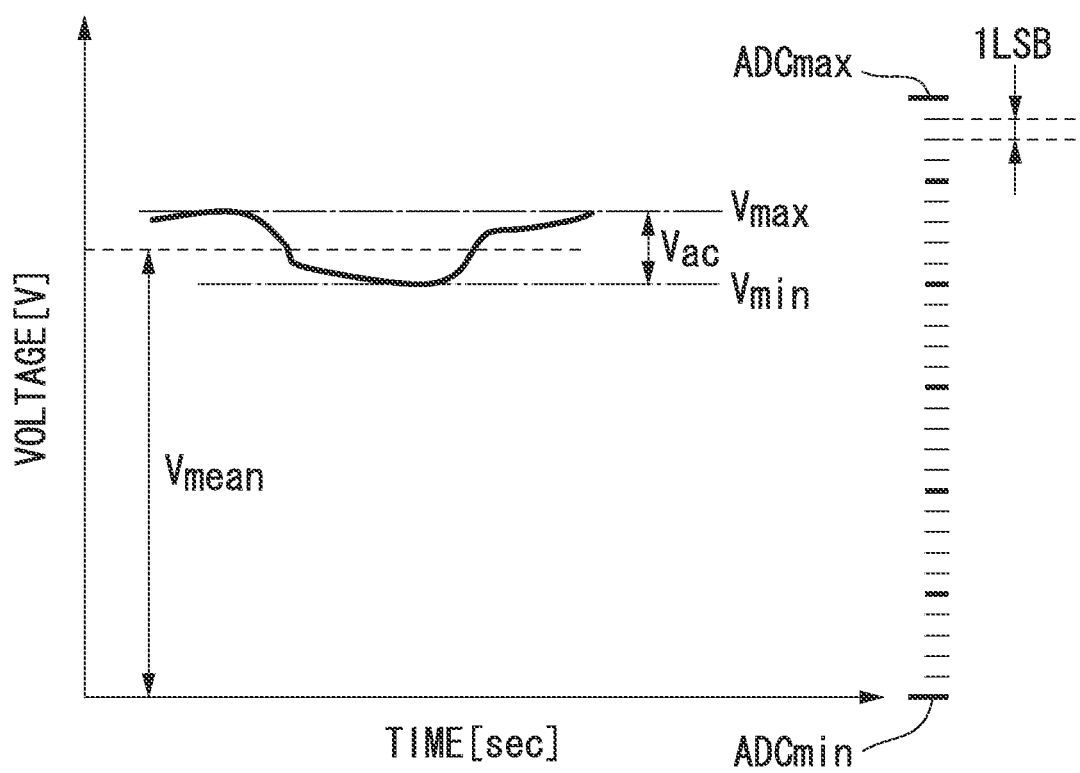
FIG. 12 is a timing chart illustrating variation of an impedance signal of heart acquired by a bioelectrical impedance measuring apparatus in accordance with the related art.

Hereinafter, an operation of adjusting the correction voltage Vcomp by the control unit CPU will be described with reference to FIGS. 9, 10A, 10B and 10C. FIG. 9 shows a sequence of reference voltage adjustment performed by the control unit CPU. In addition, FIGS. 10A, 10B and 10C show waveforms of the impedance-varying voltage VZ_AC in the respective steps shown in FIG. 9.

Step S1

When the bioelectrical impedance measuring apparatus BZ_MEAS is connected to the living body ORG to start an operation thereof, the control unit CPU outputs the correction voltage Vcomp and the amplitude control signal AMP_SIG, which are optimal to detect the impedance average voltage Vmean and the impedance-varying voltage Vac of a patient's living body. When the operation is completed, step S2 is performed.

Step S2

The control unit CPU receives the AD-conversion result AD_VAL for a predetermined time (a time longer than one cycle of the impedance variation of the living body) to store the result in a memory of the control unit CPU. When the operation is completed, step S3 is performed.

Step S3

The control unit CPU determines whether the AD-conversion result AD_VAL stored in the memory reaches an upper limit ADC_MAX of an AD convertible voltage of the AD converter ADC. If a value of the AD-conversion result AD_VAL reaches the upper limit ADC_MAX of the AD convertible voltage (for example, when a waveform L1 of FIG. 10A can be obtained), step S4 is performed. When the value of the AD-conversion result AD_VAL does not reach the upper limit ADC_MAX of the AD convertible voltage (for example, a waveform L2 of FIG. 10A can be obtained), step S5 is performed.

Step S4

The control unit CPU reduces the correction voltage Vcomp applied to the amplification unit AMPB by a predetermined rate with respect to the existing voltage. As the control is performed, for example, the waveform L1 of FIG. 10A is varied to the waveform L2, and the center voltage of the variation is decreased. When the operation is completed, the process returns to step S2.

Step S5

The control unit CPU determines whether or not the value of the AD-conversion result AD_VAL stored in the memory has reached a lower limit ADC_MIN of the AD convertible voltage of the AD converter ADC. If the value of the AD-conversion result AD_VAL reaches the lower limit ADC_MIN of the AD convertible voltage (for example, when a waveform L3 of FIG. 10B can be obtained), step S6 is performed. When the value of the AD-conversion result AD_VAL does not reach the lower limit ADC_MIN of the AD convertible voltage (for example, when a waveform L4 of FIG. 10B can be obtained), step S7 is performed.

Step S6

The control unit CPU increases the amplitude control signal AMP_SIG to reduce the constant current I_const by a predetermined rate with respect to the existing current. As the control is performed, the waveform L3 of FIG. 10B is varied to the waveform L4 to reduce the amplitude of the signal. When the operation is completed, the process returns to step S2.

Step S7

The control unit CPU determines whether the value of the AD-conversion result AD_VAL stored in the memory has a sufficient amplitude. If the value of the AD-conversion result AD_VAL is varied by only several LSBs and the impedance-varying voltage Vac cannot be AD-converted with sufficient resolution (for example, a waveform L5 of FIG. 10C can be obtained), step S8 is performed. When the value of the AD-conversion result AD_VAL is greatly varied and the impedance-varying voltage Vax can be AD-converted with sufficient resolution (for example, a waveform L6 of FIG. 10C can be obtained), the control sequence is completed.

Step S8

The control unit CPU reduces the amplitude control signal AMP_SIG to increase the constant current I_const by a predetermined rate with respect to the existing current. As the control is performed, the waveform L5 of FIG. 10C is varied to the waveform L6 to increase the amplitude of the signal. When the operation is completed, the process returns to step S2.

According to the above sequence, in a state in which the variation component of the bioelectrical impedance has a sufficient amplitude, the amplitude may be within the input voltage range (the dynamic range) of the AD converter ADC.

Hereinafter, a method of calculating an impedance value of the control unit CPU will be described. The control unit CPU calculates the impedance average value signal Zmean and the impedance-varying signal Zac from the correction voltage Vcomp, the average voltage Vave and the amplitude control signal AMP_SIG. When equation (9) is transformed, the impedance average voltage Vmean is represented as the following equation (11).

$$V_{mean} = V_{comp} - \left(1 + \frac{R_{in}}{R_f}\right)V_{ave} \quad (11)$$

Accordingly, the impedance average value signal Zmean can be obtained from Ohm's Law by the following equation (12):

$$Zmean = V\text{mean}/I\text{const} \quad (12)$$

In addition, equation (1) is substituted into equation (12) to obtain the following equation (13).

$$Zmean = V\text{mean}/\{(VDDAMP\_SIG) \times R\_\text{const}\} \quad (13)$$

In a similar way, the impedance-varying signal Zac is provided in the following equation (14):

$$Zac = Vac/\{(VDDAMP\_SIG) \times R\_\text{const}\} \quad (14)$$

As described above, according to the bioelectrical impedance measuring apparatus BZ_MEAS of the preferred embodiment, the control unit CPU can adjust the inspection current Ic and the correction voltage Vcomp such that the impedance-varying signal VZ_AC of the living body is within the input voltage range of the AD converter ADC. Thereby, the impedance-varying voltage Vac can be amplified with a high gain. Accordingly, even when the number of effective bits of the AD converter ADC is small, the average value signal Zmean of the bioelectrical impedance and the variation component signal Zac of the bioelectrical impedance can be calculated with sufficient resolution.

As can be seen from equation (15) representing the power consumption Pd of the AD converter, when the number of effective bits is small, since the AD converter ADC is operated with a low power consumption, the power consumption of the bioelectrical impedance measuring apparatus BZ_MEAS can be reduced.

$$P_d \propto f_C \times 2^{ENOB} \quad (15)$$

Accordingly, the average and variation values of the bioelectrical impedance can be precisely detected while realizing a low power consumption. In addition, since a signal component of a desired band can be removed with a lowpass filter, the impedance-varying signal VZ_AC can be more precisely obtained.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the invention is not to be considered as being limited by the foregoing description, and is only limited by the scope of the claims.

What is claimed is:

1. A bioelectrical impedance measuring apparatus comprising:
    an impedance measuring unit configured to provide an inspection current based on a predetermined current to a living body, and obtain an inspection voltage corresponding to an impedance of the living body;
    an amplification unit configured to amplify the inspection voltage with reference to a correction voltage;
    an AD converter configured to AD-convert an output of the amplification unit; and
    a control unit configured to control the inspection current and the correction voltage based on an AD-converted result of the AD converter such that the output of the amplification unit is within an input dynamic range of the AD converter, and calculate an impedance average of the living body and an impedance variation of the living body based on the predetermined current, the correction voltage and the AD-converted result.

2. The bioelectrical impedance measuring apparatus according to claim 1, wherein the amplification unit comprises a lowpass filter.

3. The bioelectrical impedance measuring apparatus according to claim 2, wherein the impedance measuring unit comprises:
    a modulation circuit configured to modulate the predetermined current into a modulated signal having a modulation frequency higher than a variable frequency of a bioelectrical impedance to generate the inspection current; and
    a demodulation circuit configured to demodulate a measurement voltage that can be obtained by applying the inspection current to the living body to generate the inspection voltage, and
    wherein the lowpass filter has a cutoff frequency smaller than twice the modulation frequency of the modulation circuit and larger than the variable frequency of the bioelectrical impedance.

4. The bioelectrical impedance measuring apparatus according to claim 2, wherein the amplification unit comprises:
    a first operational amplifier having a first non-inversion input terminal, a first inversion input terminal and a first output terminal, the inspection voltage being input into the first non-inversion input terminal, to which the first inversion input terminal and the first output terminal are connected;
    a second operational amplifier having a second non-inversion input terminal, a second inversion input terminal and a second output terminal, the correction voltage being input into the second non-inversion input terminal;
    an input resistor having a first terminal and a second terminal, the first terminal being connected to the first output terminal of the first operational amplifier and the second terminal being connected to the second inversion input terminal of the second operational amplifier;
    a feedback resistor having a third terminal and a fourth terminal, the third terminal being connected to the second inversion input terminal of the second operational amplifier and the fourth terminal being connected to the second output terminal of the second operational amplifier; and
    a feedback capacitor having a fifth terminal and a sixth terminal, the fifth terminal being connected to the second inversion input terminal of the second operational amplifier and the sixth terminal being connected to the second output terminal of the second operational amplifier.

* * * * *